(12) United States Patent
Boday et al.

(10) Patent No.: US 9,580,537 B1
(45) Date of Patent: Feb. 28, 2017

(54) DIAMINE DIONE POLYALKYL AMINE SYNTHESIS

(71) Applicant: International Business Machines Corporation, Armonk, NY (US)

(72) Inventors: Dylan J. Boday, Tucson, AZ (US); Jeannette M. Garcia, San Leandro, CA (US); James L. Hedrick, Pleasanton, CA (US); Robert J. Ono, San Jose, CA (US); Rudy J. Wojtecki, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/932,614

(22) Filed: Nov. 4, 2015

(51) Int. Cl.
| | |
|---|---|
| *C08G 12/06* | (2006.01) |
| *C08G 12/08* | (2006.01) |
| *C07C 251/04* | (2006.01) |
| *C07C 251/18* | (2006.01) |
| *C07C 251/24* | (2006.01) |

(52) U.S. Cl.
CPC ............ *C08G 12/06* (2013.01); *C07C 251/04* (2013.01); *C07C 251/18* (2013.01); *C07C 251/24* (2013.01); *C08G 12/08* (2013.01); *C07C 2101/14* (2013.01)

(58) Field of Classification Search
CPC ..................................................... C08G 12/06
USPC ......................................................... 528/266
See application file for complete search history.

(56) References Cited

U.S. PATENT DOCUMENTS

| | | | |
|---|---|---|---|
| 4,504,582 | A | 3/1985 | Swann |
| 5,466,565 | A | 11/1995 | Shigemon et al. |
| 7,276,570 | B2 | 10/2007 | Kuntimaddi et al. |
| 8,088,437 | B2 | 1/2012 | Lee et al. |

OTHER PUBLICATIONS

Mallakpour et al., "Ultrasonic assisted organo-modification of mesoporous SBA-15 with N-trimellitylimido-L-methionine and preparation of the poly(amide-imide)/SBA nanocomposites" Progress in Organic Coatings vol. 78, Jan. 2015, pp. 300-306.

Mallakpour et al., "Novel Bioactive Chiral Poly(amide-imide)s Containing Different Amino Acids Linkages: Studies on Synthesis, Characterization and Biodegradability", Journal of Polymers and the Environment, vol. 21, Issue 2, Jun. 2013, pp. 568-574.

Chong-Su Cho, "Design and Development of Degradable Polyethylenimines for Delivery of DNA and Small Interfering RNA: An Updated Review", International Scholarly Research Notices Materials Science, vol. 2012 (2012), Article ID 798247, 32 pages.

*Primary Examiner* — Duc Truong
(74) *Attorney, Agent, or Firm* — Patterson + Sheridan, LLP

(57) ABSTRACT

Methods, compounds, and compositions described herein generally relate to polyalkylamines and syntheses thereof. In some embodiments, a chemical compound has the formula:

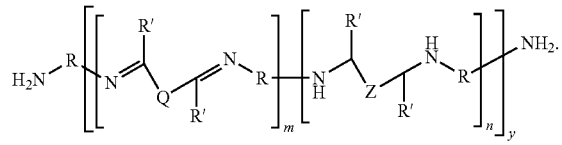

Each instance of R is independently selected from the group consisting of aryl, alkyl, and polyether. Each instance of R' is independently selected from the group consisting of hydrogen, alkyl, aryl, cycloalkyl, polyether, and alcohol. Each instance of Q and Z is independently a covalent bond or selected from the group consisting of alkyl and aralkyl.

17 Claims, No Drawings

DIAMINE DIONE POLYALKYL AMINE SYNTHESIS

FIELD

Embodiments described herein generally relate to polyalkylamines and syntheses thereof.

BACKGROUND

Gene therapy is a treatment utilized to treat diseases such as varieties of cancers, cystic fibrosis, Parkinson's disease, Alzheimer's disease, and AIDS. Gene therapy operates by transferring genetic material to target cells. Although a promising therapeutic strategy, gene therapy is limited by toxicity and efficiency of gene delivery systems.

Polyamines are used in many areas of materials engineering (such as detergents, water treatment agents, and cosmetics) with applications ranging from biomedicine to structural resins. One class of gene delivery agents involves polyethylene amines (PEIs). PEIs can condense DNA into nanoscale packages that allow easy cellular uptake. PEIs are potent gene delivery agents due to their pH buffering capacity, allowing PEIs to escape the endosomal barrier avoiding lysosomal degradation. However, the pharmacokinetic properties of PEIs render state of the art PEIs too toxic for clinical applications. PEIs that do not degrade instead accumulate in vivo, resulting in cytotoxicity. Degradation of PEIs may reduce toxicity by allowing for elimination of degraded small molecular weight metabolites through an excretion pathway. Degradation also assists in release of gene cargo being transported by a PEI.

Lower molecular weight PEIs and branched PEIs have lower cytotoxicity as compared to their higher molecular weight PEI counterparts. To promote degradability, small molecular weight PEIs may be cross-linked using degradable cross-linkers. However, incorporating some cross-linkers into a PEI chain may compromise gene delivery efficacy.

PEIs may be linear or branched. As shown in Scheme 1, linear PEIs may be synthesized by ring-opening cationic polymerization of functional, e.g. ethyl functionalized, oxazoline monomers to yield polyoxazolines. Subsequent hydrolysis of the polyamide intermediate yields linear PEIs with terminal amine moieties.

Scheme 1

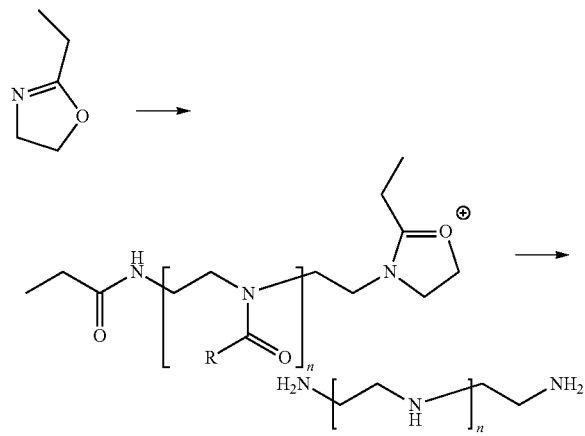

The amine spacing in the PEI product is limited, however, by (1) the number of carbon atoms in the oxazoline ring and (2) the oxazoline ring strain. Furthermore, these polymers tend to be expensive and have limited solubility.

As shown in Scheme 2, branched PEIs may be synthesized by ring-opening polymerization of aziridine monomers.

Scheme 2

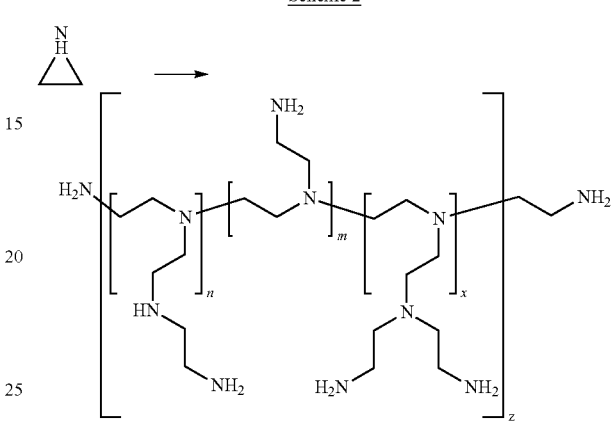

Depending on the reaction conditions, different degrees of branching may be realized along with terminal amine moieties. As with linear PEIs, the synthesis of branched PEIs is also limited by the number of carbon atoms of the aziridine monomers as well as the ring strain of the aziridine monomers. Branched PEIs are more soluble in a wide range of solvents and less expensive than linear PEIs. However, the large number of terminal amine moieties on branched PEIs renders branched PEIs unfavorably toxic.

Therefore, there is a need in the art for PEI analogs that have maintained or improved efficacy for various applications and, for clinical applications, have favorable toxicity. There is also a need in the art for improved syntheses of polyalkylamines and PEI analogs.

SUMMARY

Embodiments described herein generally relate to polyalkylamines and syntheses thereof.

The present disclosure describes a class of chemical compounds having the formula:

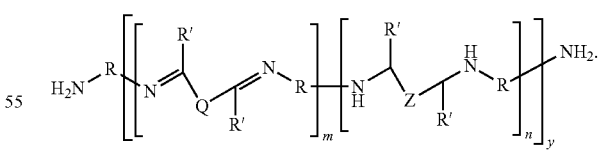

and mixtures thereof, wherein each instance of R is independently selected from the group consisting of aryl, alkyl, and polyether. Each instance of R' is independently selected from the group consisting of hydrogen, alkyl, aryl, cycloalkyl, polyether, and alcohol. Each instance of Q and Z may be independently a covalent bond or selected from the group consisting of alkyl and aralkyl. Each instance of "m" may be a positive integer. Each instance of "n" may be a positive integer, and "y" may be a positive integer.

The present disclosure further describes a class of chemical compounds having the formula:

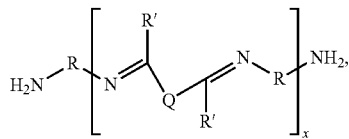

and mixtures thereof, wherein each instance of R may be independently selected from the group consisting of aryl, alkyl, and polyether. Each instance of R' may be independently selected from the group consisting of hydrogen, alkyl, aryl, cycloalkyl, polyether, and alcohol. Each instance of Q may be independently a covalent bond or selected from the group consisting of alkyl and aralkyl. "x" may be a positive integer.

DETAILED DESCRIPTION

Embodiments described herein generally relate to polyalkylamines and syntheses thereof.

The present disclosure describes a class of chemical compounds having the formula (A):

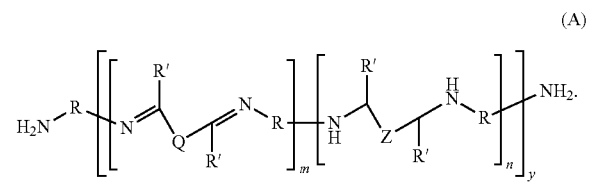

Each instance of R is independently selected from the group consisting of aryl, alkyl, and polyether. Each instance of R' is independently selected from the group consisting of hydrogen, alkyl, aryl, cycloalkyl, polyether, and alcohol. Each instance of Q and Z may be independently a covalent bond or selected from the group consisting of alkyl and aralkyl. Each instance of "m" may be a positive integer, such as between about 1 to about 200, such as about 2 to about 100. Each instance of "n" may be a positive integer, such as between about 1 to about 200, such as about 2 to about 100. "y" may be a positive integer, such as between about 1 to about 200, such as about 2 to about 100. In some embodiments, one or more of the R groups is C2-alkyl, one or more of the R' groups is H, and one or more of the Q groups is a covalent bond. In some embodiments, one or more of the R groups is an aryl independently selected from the group consisting of benzyl, phenyl, naphthyl, or heteroaryl. In some embodiments, one or more of the R groups is independently selected from C1-C10 alkyl. In some embodiments, one or more of the R groups is a polyether that is independently polyethylene glycol or polypropylene oxide. In some embodiments, one or more of the R' groups is hydrogen. In some embodiments, one or more of the R' groups is an aryl independently selected from the group consisting of benzyl, phenyl, naphthyl, or heteroaryl. In some embodiments, one or more of the R' groups is a cycloalkyl that is independently cyclopentyl or cyclohexyl. In some embodiments, one or more of the R' groups is an alcohol that is independently alkylalcohol or polyetheralcohol. In some embodiments, one or more of the R' groups is independently C1-C10 alkyl. In some embodiments, one or more of the R' groups is a polyether that is independently polyethylene glycol or polypropylene oxide. In some embodiments, one or more of the Q and Z groups is independently C1-C10 alkyl. In some embodiments, one or more of the Q and Z groups is a covalent bond. In some embodiments, a chemical compound of Formula (A) is a salt.

The present disclosure further describes a class of chemical compounds embraced by the formula (B):

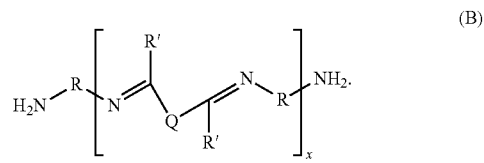

(B). Formula (B) may be considered similar to Formula (A), wherein n=0. For formula (B), one or more of the R groups may be independently selected from the group consisting of aryl, alkyl, and polyether. one or more of the R' groups may be independently selected from the group consisting of hydrogen, alkyl, aryl, cycloalkyl, polyether, and alcohol. One or more of the Q groups may be independently a covalent bond or selected from the group consisting of alkyl and aralkyl. "x" may be a positive integer, such as between about 1 to about 200, such as about 5 to about 100. In some embodiments, x is between about 35 to about 45. In some embodiments, one or more of the R groups is an aryl independently selected from the group consisting of benzyl, phenyl, naphthyl, or heteroaryl. In some embodiments, one or more of the R groups is independently C1-C10 alkyl. In some embodiments, one or more of the R groups is a polyether that is independently polyethylene glycol or polypropylene oxide. In some embodiments, one or more of the R' groups is hydrogen. In some embodiments, one or more of the R' groups is aryl independently selected from the group consisting of benzyl, phenyl, naphthyl, or heteroaryl. In some embodiments, one or more of the R' groups is cycolalkyl that is independently cylcopentyl or cyclohexyl. In some embodiments, one or more of the R' groups is alcohol that is independently alkylalcohol or polyetheralcohol. In some embodiments, one or more of the R' groups is independently C1-C10 alkyl. In some embodiments, one or more of the R' groups is a polyether that is independently polyethylene glycol or polypropylene oxide. In some embodiments, one or more of the Q groups is independently C1-C10 alkyl. In some embodiments, one or more of the Q groups is a covalent bond. In some embodiments, one or more of the R groups is C2-alkyl, one or more of the R' groups is H, and one or more of the Q groups is a covalent bond. In some embodiments, a chemical compound of Formula (B) is a salt.

The present disclosure further describes salts of the chemical compounds of Formula (A) and Formula (B). As described herein, the term "salt" refers to a salinified form of a compound, such as where one or more cations (such as Na+) and/or one or more anions (such as Cl−) couples with one or more cationic and/or one or more anionic forms of a chemical compound of Formula (A) and/or Formula (B). Examples of salts include acid addition salts formed with inorganic or organic acids, metal salts, and amine salts. Examples of acid addition salts formed with inorganic acids include salts with hydrochloric acid, hydrobromic acid, hydriodic acid, sulfuric acid, nitric acid and phosphoric acid.

Examples of acid addition salts formed with organic acids include acetic acid, trifluoroacetic acid, propionic acid, hexanoic acid, heptanoic acid, cyclopentanepropionic acid, glycolic acid, pyruvic acid, lactic acid, citric acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, glucoheptonic acid, 4,4'-methylenebis(3-hydroxy-2-naphthoic) acid, 3-phenylpropionic acid, trimethylacetic acid, tertiary butylacetic acid, lauryl sulfuric acid, gluconic acid, glutamic acid, hydroxynaphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases (e.g., cytosine, thymine, uracil and guanine).

Compounds, compositions, and methods described herein generally relate to polyalkylamines that may be synthesized via polycondensation of α,ω-diamines and diketones/dialdehydes to form polyimines. A portion or all of a polyimine may be reduced (e.g., reductive amination). As described herein, a polyalkylamine is a partially unsaturated polymer containing both imine and amine linkages within the polymer backbone. In embodiments herein where only a portion of a polyimine has been reduced, the resulting polyalkylamine possesses dynamic covalent character by virtue of reversible imine linkages within the polyalkylamine backbone. Dynamic covalent imine linkages impart biodegradability of the polyalkylamine when the polyalkylamine is used, for example, as a gene therapy agent. Furthermore, polyalkylamines described herein possess improved solubility, among other properties, as compared to linear PEI. Polyalkylamines described herein possess the same or improved utility as compared to typical PEI applications, such as a gene therapy agent.

In some embodiments, polyalkylamines (and polyimines) described herein may be a component of a composition, such as a pharmaceutical composition, wherein a polyalkylamine and/or polyimine is present in a composition in a therapeutically effective amount for, for example, gene therapy. As described herein, the term "therapeutically effective amount" refers to an amount of a compound that, when administered to a subject for treating a condition, is sufficient to effect treatment for the condition. "Therapeutically effective amount" can vary depending on the compound, the disease and its severity, the age, the weight, etc. of the subject to be treated. Compositions may include, for example, one or more genes and/or one or more anti-cancer drugs. Anti-cancer drugs include, for example, alkylating agents, anti-metabolites, plant alkaloids and terpenoids, topoisomerase inhibitors, cytotoxic antiobiotics, angiogenesis inhibitors and tyrosine kinase inhibitors.

Scheme 3 illustrates polyalkylamine synthesis according to some embodiments of the present disclosure. As shown in Scheme 3, polycondensation of α,ω-diamine and diketone/dialdehyde yields a polyimine. The R group of the α,ω-diamine may be hydrophobic or hydrophilic. In some embodiments, the R group of the α,ω-diamine is aryl, alkyl, or polyether. In some embodiments, aryl is benzyl, phenyl, naphthyl, or heteroaryl. In some embodiments, alkyl is any species of C1-C10 alkyl. In some embodiments, polyether is polyethylene glycol or polypropylene oxide.

In some embodiments, the R' group of the diketone/dialdehyde is hydrogen, alkyl, aryl, cycloalkyl, polyether, alcohol, or a mixture thereof. Aryl may be benzyl, phenyl, naphthyl, or heteroaryl. Alkyl may be any species of C1-C10 alkyl. Polyether may be polyethylene glycol or polypropylene oxide. Cycloalkyl may be substituted or unsubstituted cyclopentyl or substituted or unsubstituted cyclohexyl. Alcohol may be alkylalcohol or polyetheralcohol. Furthermore, although Scheme 3 shows a 1,2-diketone/dialdehyde, a variety of diones and dialdehydes may be used for polyimine formation. Diketones/dialdehydes include alkyl diketones/dialdehydes including 1,2-, 1,3-, 1,4-, 1,5-, 1,6-, 1,7-, 1,8-, 1,9-, and 1,10-diketones/dialdehydes. A diketone/dialdehyde may also be aralkyl. As described herein, the term "aralkyl" embraces an aryl-substituted alkyl radical and may be used interchangeably with the term "arylalkyl". Examples of aralkyl include benzyl, diphenylmethyl, triphenylmethyl, phenylethyl and diphenylethyl. Whereas linear PEI is inherently limited in structure and scope due to the oxazoline monomeric starting material and branched PEIs are inherently limited in structure and scope due to the aziridine monomeric starting material, polyalkylamine syntheses described herein allow for a diverse array of functionality on the polyimine backbone and polyalkylamine backbone as well as control of the amine spacing of the polyimine backbone and polyalkylamine backbone. The ability to tailor the polyimine backbone and polyalkylamine backbone enables, for example, structure activity determinations for pharmaceutical applications. Such structure activity determinations may include toxicity, solubility, and gene delivery, among others.

In some embodiments, a polyimine may be synthesized by reacting an α,ω-diamine and a diketone/dialdehyde under neat conditions (e.g., not in the presence of a solvent). In some embodiments, a polyimine may be synthesized by reacting an α,ω-diamine and a diketone/dialdehyde in a solvent, such as an organic solvent, and/or an acid catalyst with a Dean-Stark apparatus. Solvent(s) may be removed in vacuo after completion of polyimine formation. Organic solvents include polar aprotic solvents such as dimethylamino pyridine (DMAP), dimethyl formamide (DMF), benzene, dimethylsulfoxide (DMSO), or tetrahydrofuran (THF). The absence of an acid catalyst for polyimine formation allows, for example, the subsequent reductive amination of the polyimine to be carried out without isolating the polyimine product before the reductive amination. In some embodiments, reductive amination of a polyimine is carried out without isolating the polyimine product before reductive amination, even though an acid catalyst was utilized in a polyimine formation. In some embodiments, a polyimine product is isolated from residual starting material (if present), such as diketone/dialdehyde and diamine, before a reductive amination.

reaction. Substoichiometric amounts of reducing agent result in a polyalkylamine having imine bonds and amine bonds along the backbone (i.e., a partially saturated polyalkylamine), while excess (superstoichiometric) amounts of reducing agent yield a saturated polyalkylamine having predominantly, if not exclusively, amine bonds along the backbone of the polyalkylamine reaction product. Stoichiometric amounts of reducing agent yield exclusively saturated polyalkylamine (e.g., PEI) or a mixture of partially saturated

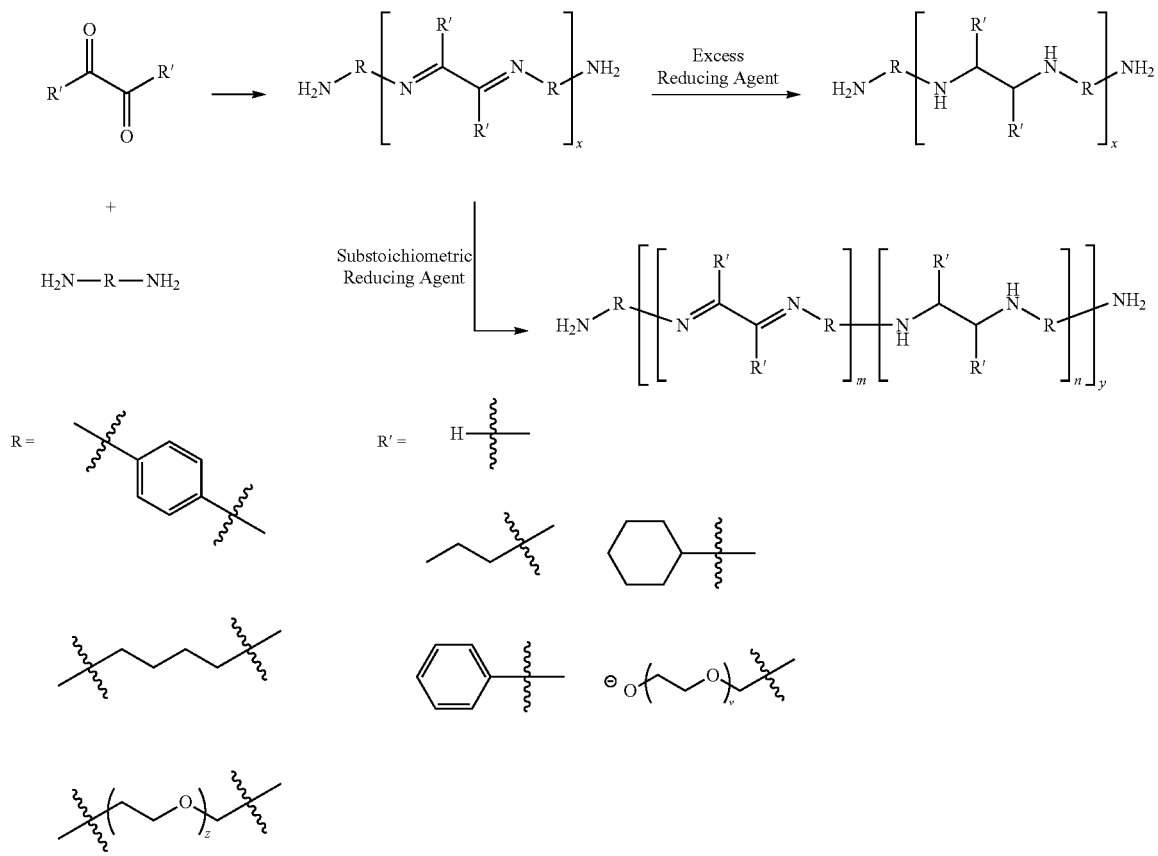

As shown in Scheme 3, a polyimine may be reduced via, for example, reductive amination. In some embodiments, reductive amination is carried out using a reducing agent, such as $NaBH_4$, $NaCNBH_3$, $NaBH(OAc)_3$, or $LiAlH_4$. The stoichiometry of the reducing agent may be used to promote complete reductive amination or partial reductive amination of a polyimine. As described herein, the term "stoichiometric" means one equivalent of reducing agent for each imine group of a polyimine backbone. For example, a polyimine having 80 imine moieties of the polyimine backbone may have 80 molar equivalents of reducing agent:polyimine to be considered a "stoichiometric" amount of reducing agent. Thus, the molecular weight of the polyimine determines the number of imine functional groups of the polyimine backbone which will determine what constitutes a "stoichiometric" amount of reducing agent for a reductive amination polyalkylamine and saturated polyalkylamine (not shown). Accordingly, the identity and stoichiometry of the reducing agent allows for control of the degradation profile of a resulting polyalkylamine. In some embodiments, "x" is a positive integer, such as between about 1 to about 200, such as about 5 to about 100. "x" may be an integer about 35 to about 45, such as about 40. In some embodiments, each instance of "m" is a positive integer, such as between about 1 to about 200, such as about 2 to about 100. In some embodiments, each instance of "n" is a positive integer, such as between about 1 to about 200, such as about 2 to about 100. "y" may be a positive integer, such as between about 1 to about 200, such as about 2 to about 100. In some embodiments, "y" is about 15 to about 25, such as about 20. In some embodiments, each instance of "z" is a positive integer, such as between about 1 to about 100, such as about 2 to about 50. In some embodiments, each instance of "v" is a positive integer, such as between about 1 to about 100, such as about 2 to about 50.

Polyimines and polyalkylamines of the present disclosure can exist in tautomeric, geometric or stereoisomeric forms. Ester, metabolite, oxime, prodrug, onium, hydrate, solvate and N-oxide forms of polyalkylamines and polyimines described herein are also embraced by the present disclosure. The present disclosure considers all such compounds, including, but not limited to, cis- and trans-geometric isomers (Z- and E-geometric isomers), R- and S-enantiomers, diastereomers, d-isomers, l-isomers, atropisomers, epimers, conformers, rotamers, mixtures of isomers and racemates thereof, as falling within the scope of the present disclosure. Some of the compounds described herein contain one or more stereocenters and are meant to include R, S and mixtures of R and S forms for each stereocenter present.

Scheme 4 illustrates the degradation (e.g., biodegradability) of a polyimine and polyalkylamine. As shown in Scheme 4, a polyimine according to some embodiments may hydrolyze in the presence of an acid (for example, the milieu of an endosome) to yield, for example, fully hydrolyzed and partially hydrolyzed byproducts. Like a polyimine, a polyalkylamine according to some embodiments may also hydrolyze in the presence of an acid to yield, for example, fully hydrolyzed and partially hydrolyzed byproducts. In, for example, gene delivery applications, degradation of a polyimine or polyalkylamine reduces toxicity (as compared to toxicity of a PEI) by allowing for elimination of the small molecular weight metabolites (produced by the hydrolysis degradation) through an excretion pathway. Lower molecular weight metabolites show lower cytotoxicity as compared to their higher molecular weight counterparts because the lower molecular weight metabolites do not accumulate in vivo, i.e. lower molecular weight metabolites allow for improved pharmacokinetic properties of polyimines and polyalkylamines as compared to the pharmacokinetic properties of PEI. Degradation also assists in release of gene cargo being transported by a polyimine or polyalkylamine.

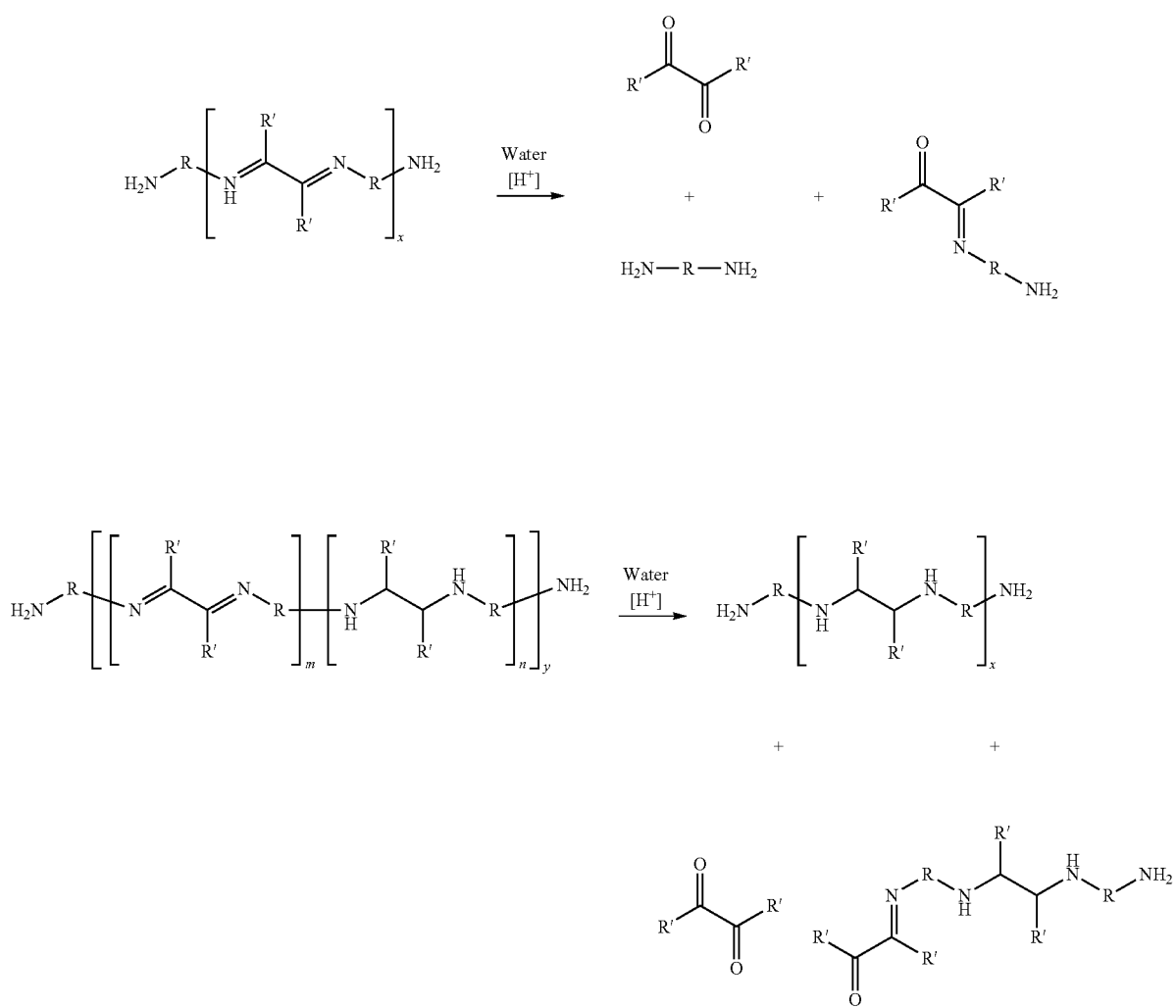

Scheme 4

Non-limiting examples of polyalkylamines of the present disclosure are shown in Table 1. The chemical compounds of Table 1 are versions of Formula (A) where Q and Z are covalent bonds in each case, R is selected from the group consisting of (-Et-O)$_z$, (—CH2-)$_4$, and phenyl, and R' is selected from the group consisting of hydrogen, n-propyl, phenyl, cyclohexyl, and (—O-Et-)$_v$OH, where every R in one molecule is the same and every R' in one molecule is the same.

TABLE 1

| Ex. # | Structure (wherein each instance of "m" is a positive integer, such as between about 1 to about 200, such as about 2 to about 100; each instance of "n" is a positive integer, such as between about 1 to about 200, such as about 2 to about 100; "y" is a positive integer, such as between about 1 to about 200, such as about 2 to about 100; each instance of "z" is a positive integer, such as between about 1 to about 100, such as about 2 to about 50; each instance of "v" is a positive integer, such as between about 1 to about 100, such as about 2 to about 50.) |
|---|---|
| 1 | 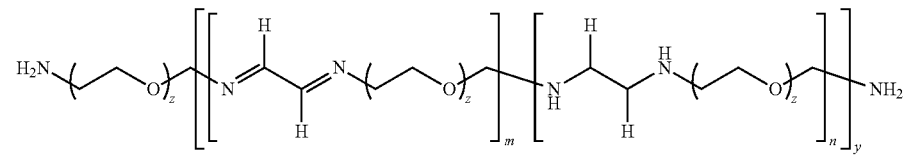 |
| 2 | 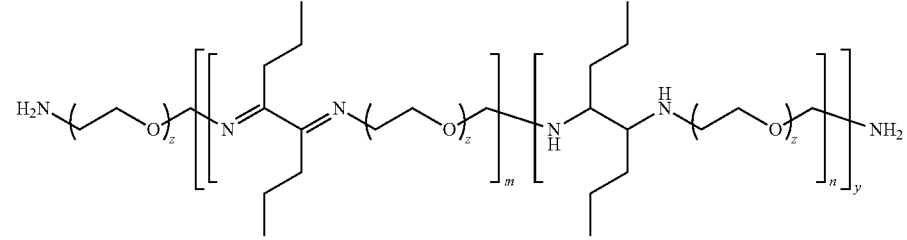 |
| 3 | 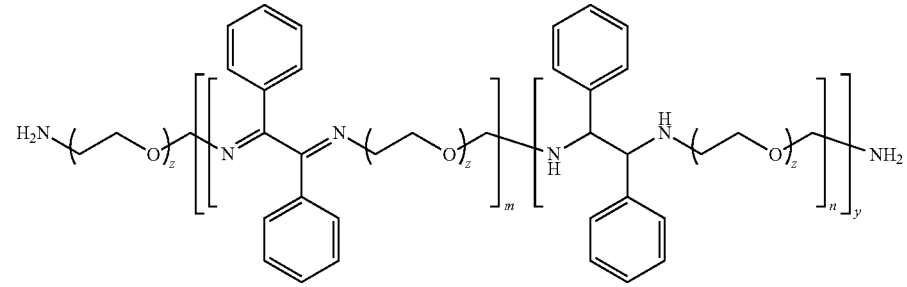 |
| 4 | 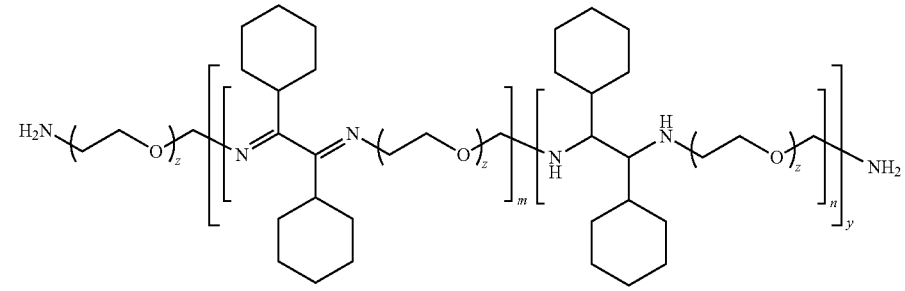 |
| 5 | 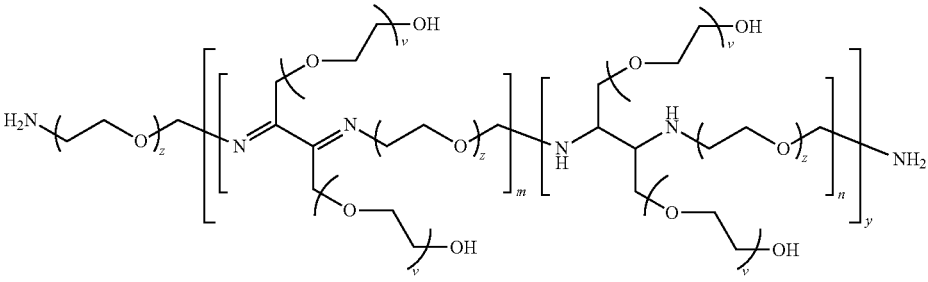 |

TABLE 1-continued

| Ex. # | Structure (wherein each instance of "m" is a positive integer, such as between about 1 to about 200, such as about 2 to about 100; each instance of "n" is a positive integer, such as between about 1 to about 200, such as about 2 to about 100; "y" is a positive integer, such as between about 1 to about 200, such as about 2 to about 100; each instance of "z" is a positive integer, such as between about 1 to about 100, such as about 2 to about 50; each instance of "v" is a positive integer, such as between about 1 to about 100, such as about 2 to about 50.) |
|---|---|
| 6 | 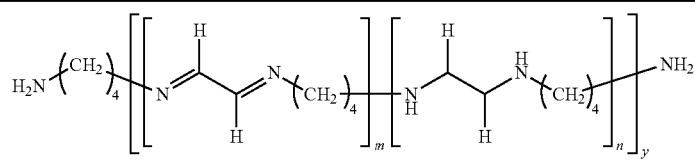 |
| 7 | 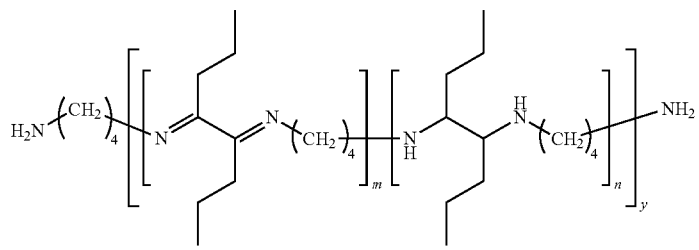 |
| 8 | 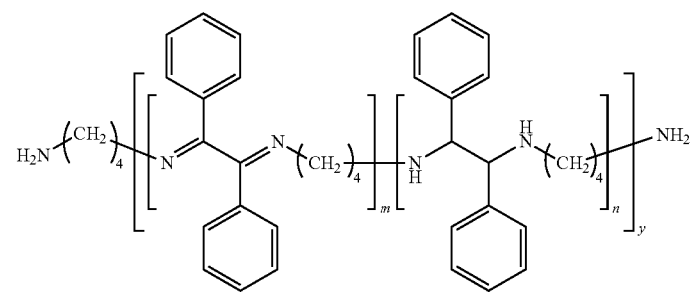 |
| 9 | 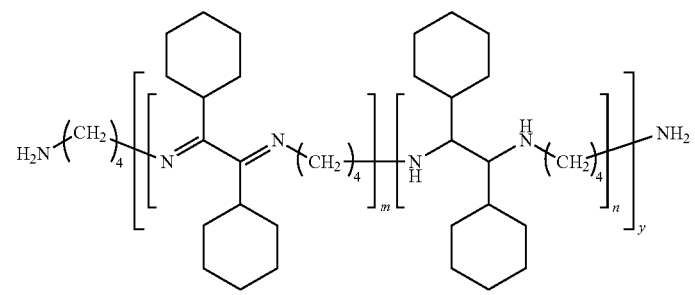 |
| 10 | 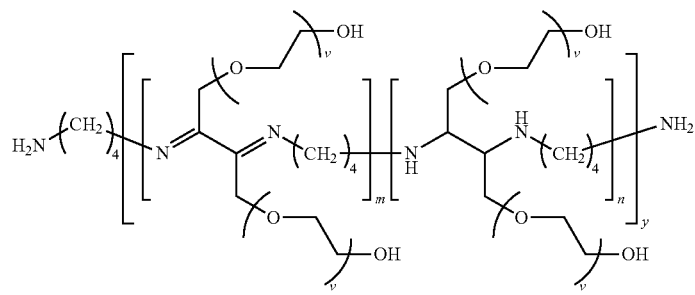 |
| 11 | 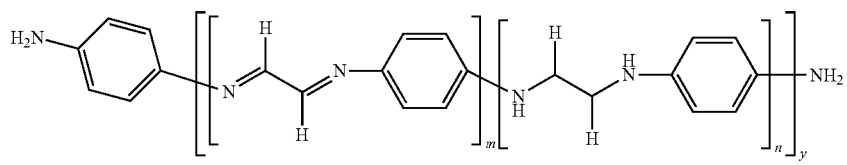 |

TABLE 1-continued

| Ex. # | Structure (wherein each instance of "m" is a positive integer, such as between about 1 to about 200, such as about 2 to about 100; each instance of "n" is a positive integer, such as between about 1 to about 200, such as about 2 to about 100; "y" is a positive integer, such as between about 1 to about 200, such as about 2 to about 100; each instance of "z" is a positive integer, such as between about 1 to about 100, such as about 2 to about 50; each instance of "v" is a positive integer, such as between about 1 to about 100, such as about 2 to about 50.) |
|---|---|
| 12 | 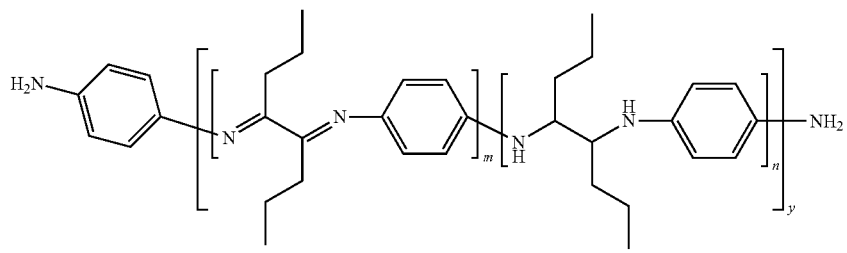 |
| 13 | 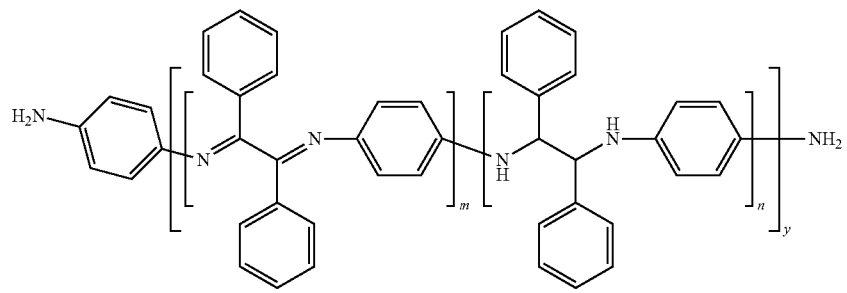 |
| 14 | 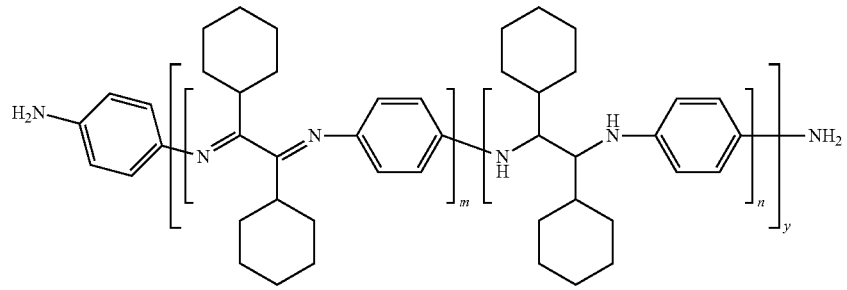 |
| 15 | 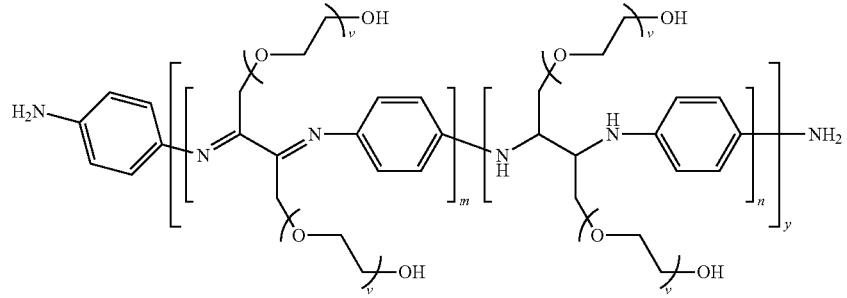 |

Non-limiting examples of polyimines of the present disclosure are shown in Table 2. The chemical compounds of Table 2 are versions of Formula (B) where Q is a covalent bond in each case, R is selected from the group consisting of (-Et-O)$_z$, (—CH2-)$_4$, and phenyl, and R' is selected from the group consisting of hydrogen, n-propyl, phenyl, cyclohexyl, and (—O-Et-)$_v$OH, where every R in one molecule is the same and every R' in one molecule is the same.

TABLE 2

Structure (wherein "x" is a positive integer, such as between about 1 to about 200, such as about 5 to about 100; each instance of "z" is a positive integer, such as between about 1 to about 100, such as about 2 to about 50; each instance of "v" is a positive integer, such as between about 1 to about 100, such as about 2 to about 50.)

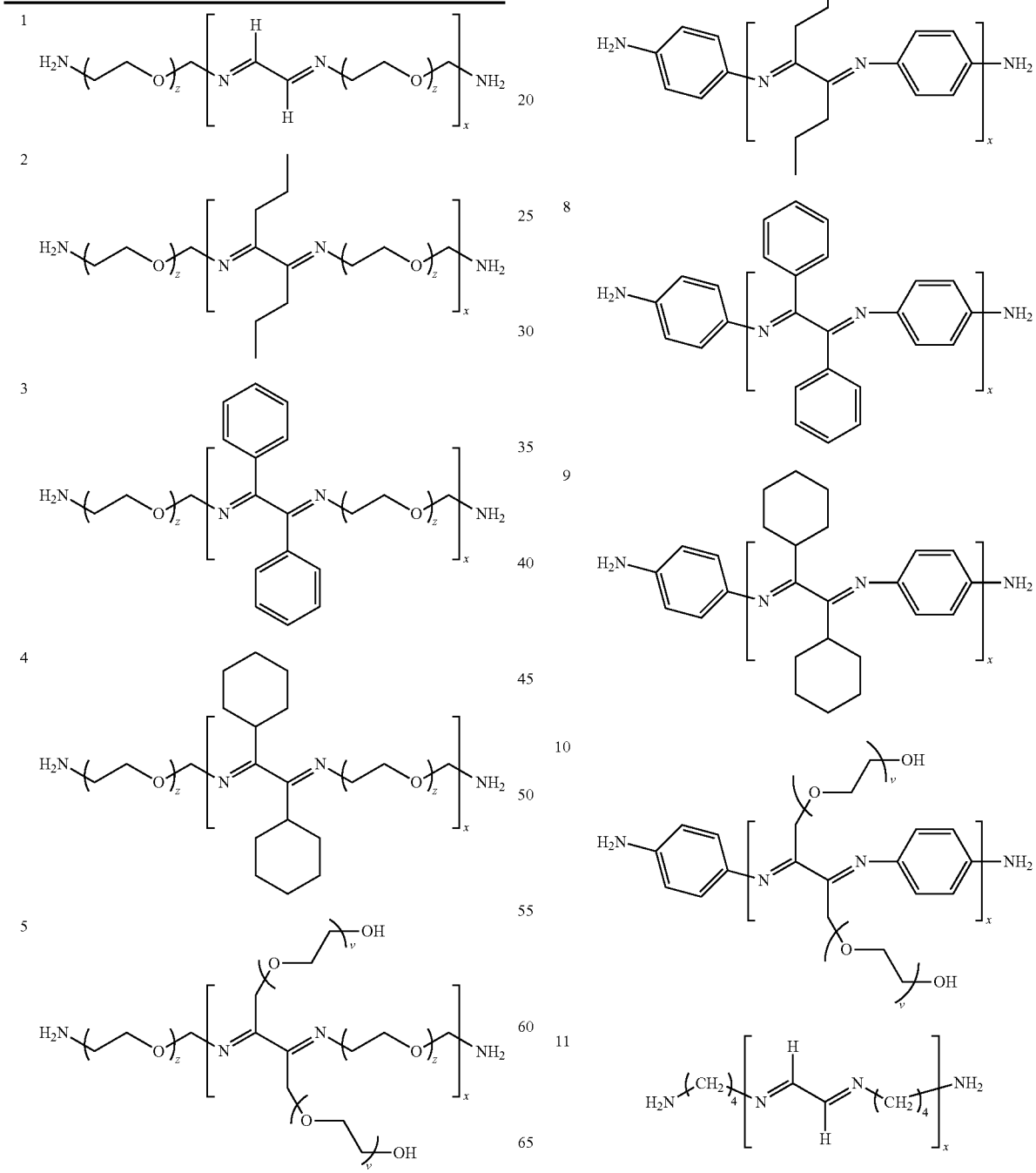

TABLE 2-continued

Structure (wherein "x" is a positive integer, such as between about 1 to about 200, such as about 5 to about 100; each instance of "z" is a positive integer, such as between about 1 to about 100, such as about 2 to about 50; each instance of "v" is a positive integer, such as between about 1 to about 100, such as about 2 to about 50.)

| Ex. # | Structure |
|---|---|
| 12 | 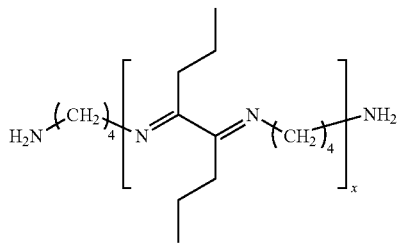 |
| 13 | 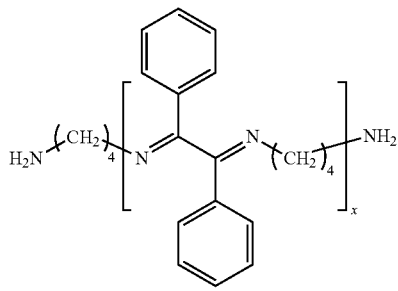 |
| 14 | 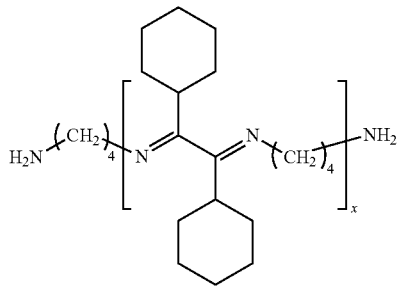 |
| 15 | 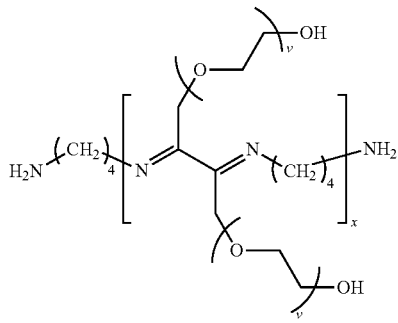 |

Note that in summarizing the tables above, the notation "Et" refers to the ethyl radical $C_2H_5$.

Overall, polyalkylamines described herein allow for dynamic covalent linkages within the polyalkylamine backbone that may be readily degraded in vivo, for example, when used in gene delivery applications. The polyalkylamines described herein possess improved solubility, among other properties, as compared to linear PEI. Polyalkylamines of the present disclosure possess the same or improved utility in typical PEI applications, such as a gene therapy agent. Furthermore, whereas linear PEI is inherently limited in structure and scope due to the oxazoline monomeric starting material and branched PEIs are inherently limited in structure and scope due to the aziridine monomeric starting material, polyalkylamine syntheses described herein allow for a diverse array of functionality on the polyimine backbone and polyalkylamine backbone as well as control of the amine spacing of the polyimine backbone and polyalkylamine backbone. For gene delivery applications, degradation of a polyimine or polyalkylamine reduces toxicity (as compared to toxicity of a PEI) by allowing for elimination of the small molecular weight metabolites (produced by the hydrolysis degradation) through an excretion pathway. Elimination of the lower molecular weight metabolites lowers accumulation of a polyimine or polyalkylamine in vivo, i.e. improved pharmacokinetic properties of polyimines and polyalkylamines as compared to the pharmacokinetic properties of PEI.

The present disclosure has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the embodiments.

What is claimed is:

1. A compound, or mixture comprising a compound, of the formula:

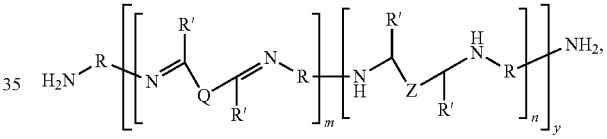

wherein each instance of R is independently selected from the group consisting of aryl, alkyl, and polyether;

wherein each instance of R' is independently selected from the group consisting of hydrogen, alkyl, aryl, cycloalkyl, polyether, and alcohol;

wherein each instance of Q and Z is independently a covalent bond or selected from the group consisting of alkyl and aralkyl;

wherein each instance of m is a positive integer;

wherein each instance of n is a positive integer; and wherein each instance of y is a positive integer.

2. The compound of claim 1, wherein at least one R is an aryl selected from the group consisting of benzyl, phenyl, naphthyl, or heteroaryl.

3. The compound of claim 1, wherein at least one R is selected from C1-C10 alkyl.

4. The compound of claim 1, wherein at least one R is a polyether selected from the group consisting of polyethylene glycol or polypropylene oxide.

5. The compound of claim 1, wherein each instance of R' is hydrogen.

6. The compound of claim 1, wherein at least one R' is an aryl selected from the group consisting of benzyl, phenyl, naphthyl, or heteroaryl.

7. The compound of claim 1, wherein at least one R' is a cycloalkyl that is cyclopentyl or cyclohexyl.

8. The compound of claim 1, wherein at least one R' is an alcohol that is alkylalcohol or polyether-alcohol.

9. The compound of claim 1, wherein at least one R' is C1-C10 alkyl.

10. The compound of claim 1, wherein each instance of R' is a polyether that is independently polyethylene glycol or polypropylene oxide.

11. The compound of claim 1, wherein each instance of Q and Z is independently C1-C10 alkyl.

12. The compound of claim 1, wherein each instance of Q and Z is a covalent bond.

13. The compound of claim 1, wherein y is between about 15 and about 25.

14. The compound of claim 1, which is selected from the group consisting of:

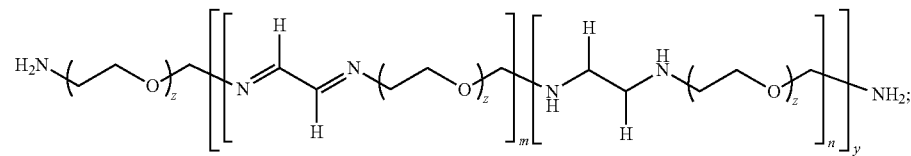

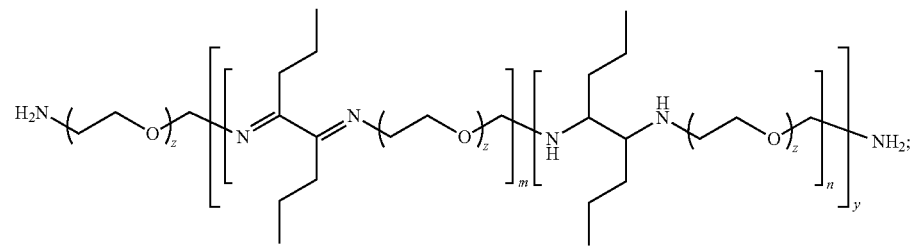

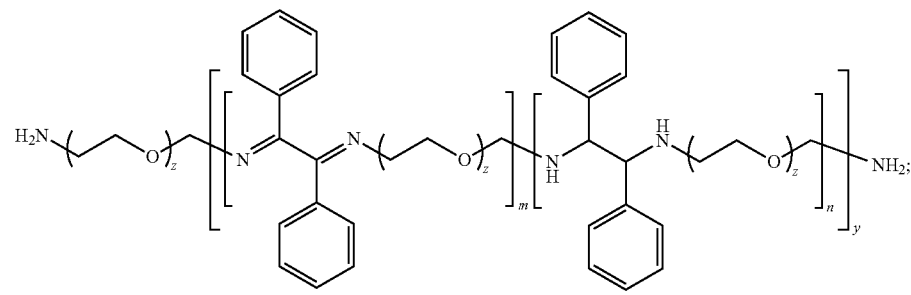

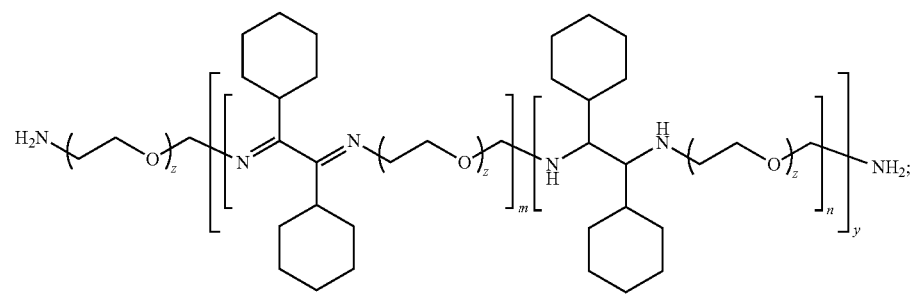

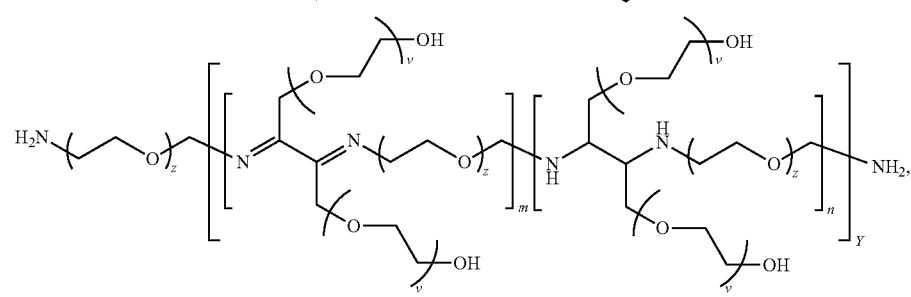

wherein each instance of z is a positive integer, and wherein each instance of v is a positive integer.
15. The compound of claim 1, which is selected from the group consisting of:
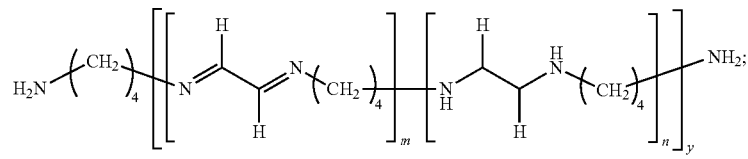
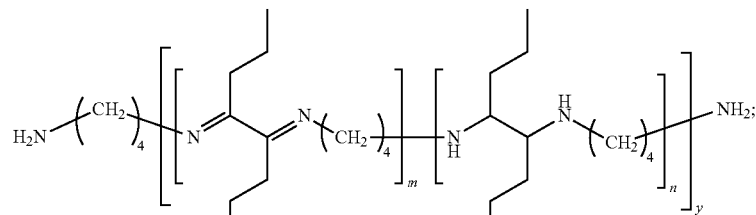
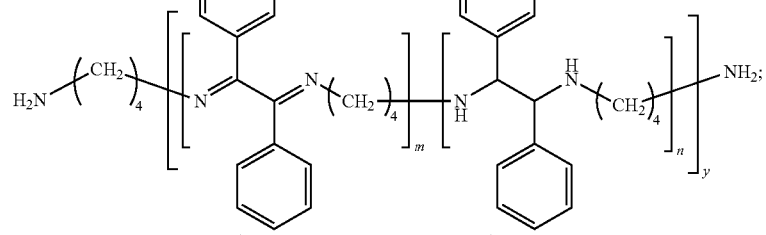
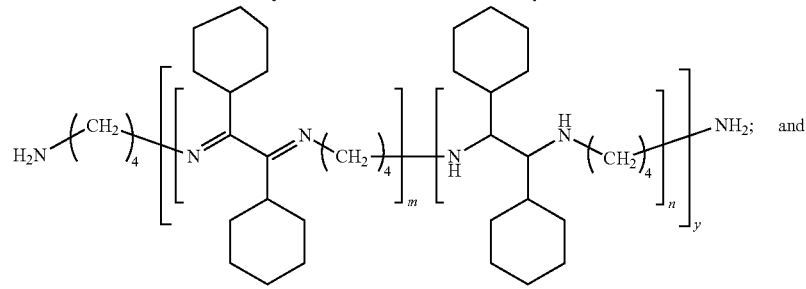
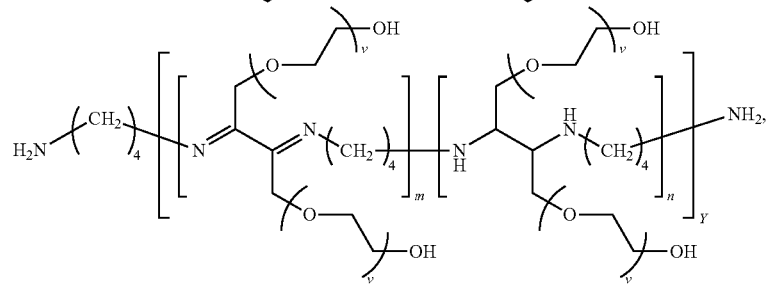
wherein each instance of v is a positive integer.
16. The compound of claim 1, which is selected from the group consisting of:
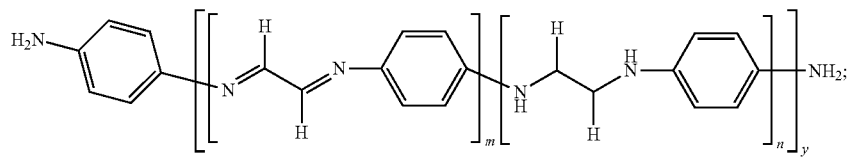

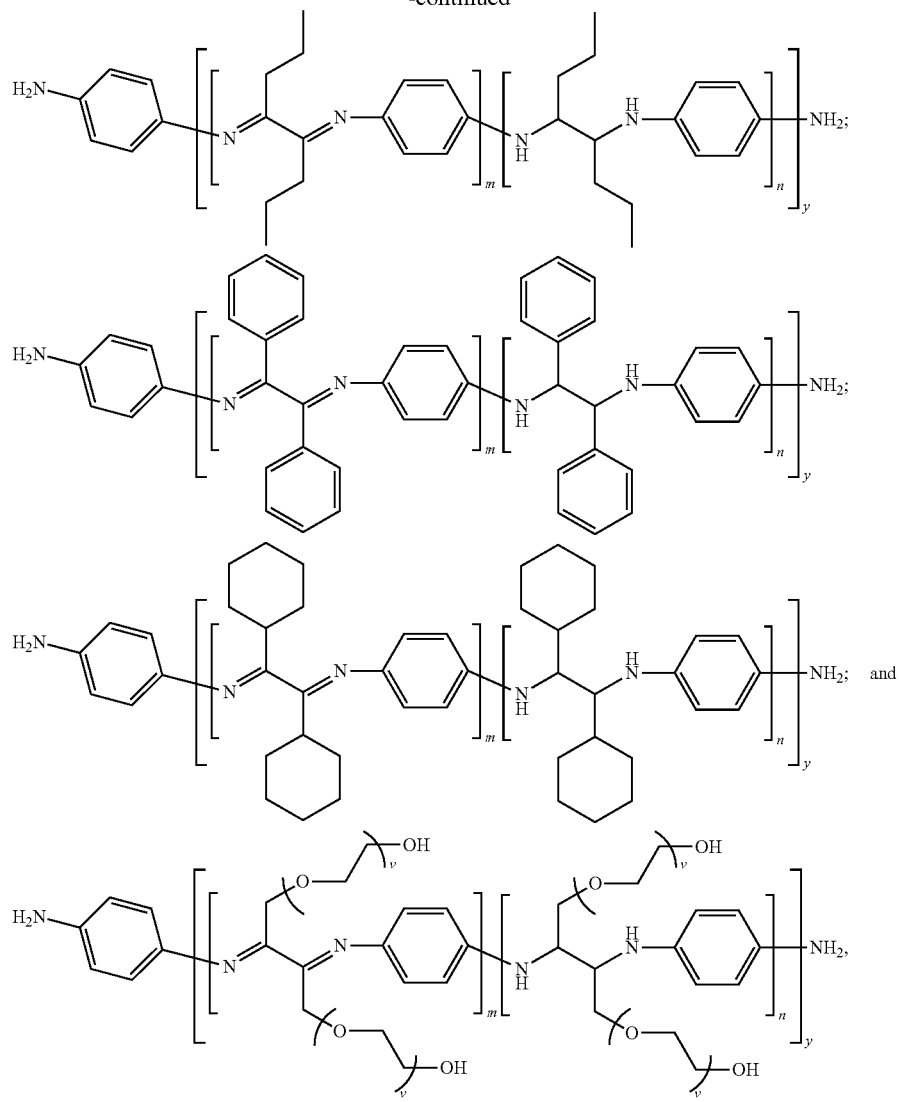
wherein each instance of v is a positive integer.
17. A salt derivative of the compound of claim 1.
* * * * *